（12） United States Patent
Mitchell

(10) Patent No.: US 10,765,549 B2
(45) Date of Patent: Sep. 8, 2020

(54) FLEXIBLE FOOT ABDUCTION APPARATUS

(71) Applicant: John R. Mitchell, Wayland, IA (US)

(72) Inventor: John R. Mitchell, Wayland, IA (US)

( * ) Notice: Subject to any disclaimer, the term of this patent is extended or adjusted under 35 U.S.C. 154(b) by 529 days.

(21) Appl. No.: 15/586,980

(22) Filed: May 4, 2017

(65) Prior Publication Data
US 2018/0318121 A1 Nov. 8, 2018

(51) Int. Cl.
*A61F 5/01* (2006.01)
*A43B 3/30* (2006.01)
*A43B 7/00* (2006.01)
*A43B 3/02* (2006.01)

(52) U.S. Cl.
CPC .............. *A61F 5/0127* (2013.01); *A43B 3/30* (2013.01); *A43B 7/00* (2013.01); *A43B 3/02* (2013.01)

(58) Field of Classification Search
CPC ..... A61F 5/0127; A61F 5/0113; A61F 5/0116
USPC ...... 602/5, 16, 23, 24, 27, 29; 128/846, 869, 128/882; 36/140, 141, 142, 143, 144
See application file for complete search history.

(56) References Cited

U.S. PATENT DOCUMENTS

| | | |
|---|---|---|
| 1,130,084 A | 3/1915 | Havens |
| 2,472,819 A | 6/1949 | Giesen |
| 2,482,646 A | 9/1949 | Brachman et al. |
| 2,585,342 A | 2/1952 | Morgan |
| 2,906,261 A | 9/1959 | Craig |
| 3,171,407 A | 3/1965 | Rogers |
| 3,188,753 A | 6/1965 | Lovercheck |
| 3,523,526 A | 8/1970 | Phelps |
| 3,777,747 A | 12/1973 | Friedman |
| 3,892,231 A | 7/1975 | Tummillo |
| 4,088,129 A | 5/1978 | DiGiulio |
| 4,249,523 A | 2/1981 | Bidwell |
| 4,303,065 A | 12/1981 | Ericson |
| 4,332,570 A | 6/1982 | Getty |
| 4,336,795 A | 6/1982 | Nichols |
| 4,412,536 A | 11/1983 | Kurtz et al. |
| 4,466,800 A | 8/1984 | Breiden |
| 4,481,940 A | 11/1984 | Kurtz et al. |
| 4,495,943 A | 1/1985 | Kurtz et al. |
| 4,520,803 A | 6/1985 | Quest |
| 4,570,620 A | 2/1986 | Kurtz et al. |

(Continued)

FOREIGN PATENT DOCUMENTS

| | | |
|---|---|---|
| DE | 20212504 | 12/2002 |
| SU | 1156116 A1 | 5/1985 |

(Continued)

OTHER PUBLICATIONS

European Search Report dated Jan. 12, 2010 from related European Application No. 09170362.9.

(Continued)

*Primary Examiner* — Anna K Kinsaul
*Assistant Examiner* — Caitlin A Carreiro
(74) *Attorney, Agent, or Firm* — Nyemaster Goode, P.C.

(57) ABSTRACT

A flexible foot abduction apparatus allowing movement in a horizontal and vertical plane with an elongated member made of a shape memory material. The elongated bar is shaped such that it has both vertical and horizontal aspects to allow a user to more easily manipulate the apparatus in one or both planes. The elongated member has an original shape which can be selectively forced into a second shape by a user and then return to the original shape.

20 Claims, 5 Drawing Sheets

(56) References Cited

U.S. PATENT DOCUMENTS

| | | | |
|---|---|---|---|
| 4,606,334 | A | 8/1986 | Salmon |
| 5,215,518 | A | 6/1993 | Rosen |
| 5,346,463 | A | 9/1994 | Devens |
| 5,382,225 | A | 1/1995 | Sutcliffe |
| 5,401,235 | A | 3/1995 | Devens |
| 5,470,310 | A | 11/1995 | Sutcliffe |
| 5,483,757 | A | 1/1996 | Frykberg |
| 5,489,258 | A | 2/1996 | Wohnsen et al. |
| 5,681,649 | A | 10/1997 | Mashita et al. |
| 5,797,200 | A | 8/1998 | Hess et al. |
| 6,094,844 | A | 8/2000 | Potts |
| 6,173,511 | B1 | 1/2001 | Perrault |
| 6,328,707 | B1 | 12/2001 | Lampkins |
| 6,582,232 | B1 | 6/2003 | Ney |
| 7,267,657 | B1 | 9/2007 | Mitchell |
| 7,569,023 | B2 | 8/2009 | Dobbs |
| 7,850,631 | B2 | 12/2010 | Mitchell |
| 7,867,184 | B2 | 1/2011 | Mitchell |
| 8,361,004 | B2 | 1/2013 | Mitchell |
| 8,641,651 | B2 | 2/2014 | Mitchell |
| 2004/0244221 | A1 | 12/2004 | Hall et al. |
| 2007/0016122 | A1 | 1/2007 | Bowman |
| 2007/0073206 | A1 | 3/2007 | Hatton et al. |
| 2007/0142760 | A1* | 6/2007 | Mitchell .............. A61F 5/0111 602/29 |
| 2007/0289170 | A1 | 12/2007 | Avent et al. |
| 2008/0064017 | A1 | 3/2008 | Grundmeyer et al. |
| 2010/0069808 | A1* | 3/2010 | Mitchell .............. A61F 5/0193 602/29 |
| 2012/0116271 | A1 | 5/2012 | Caruso et al. |

FOREIGN PATENT DOCUMENTS

| | | |
|---|---|---|
| SU | 1220010 | 3/1986 |
| WO | WO2007112962 | 10/2007 |

OTHER PUBLICATIONS

International Search Report dated Nov. 9, 2010 for related PCT Application No. PCT/US2010/049920.

"Endless Sketchbook", MoHDI, instructables.com http://web.archive.org/web/20100430102951/http://www.instructables.com/id/Endless-Sketchbook/, Apr. 30, 2010.

Mitchell, John R.—U.S. Appl. No. 12/889,621, filed Sep. 24, 2010.
Mitchell, John R.—U.S. Appl. No. 14/046,170, filed Oct. 4, 2013.
Mitchell, John R.—U.S. Appl. No. 14/925,338, filed Oct. 28, 2015.

* cited by examiner

FLEXIBLE FOOT ABDUCTION APPARATUS

BACKGROUND

Dr. Ignacio Ponseti is an internationally famous physician and surgeon specializing in the treatment and management of a childhood deformity commonly know as a club foot. Dr. Ponseti has for many decades promoted the use of a foot and ankle abduction device, or orthosis, that is used to correct and prevent relapses of the club foot deformity. These abduction devices typically consist of a rigid bar connected between shoes worn by the child which bar separates the feet of the child and holds the feet in an outward rotation or abduction. Typically, if the condition is diagnosed early enough, this device is worn full-time for a period of months, but during the period of treatment, the angle of outward rotation is periodically adjusted.

The Ponseti technique, as it has become known throughout the world, has been highly successful in treating club feet without the necessity of corrective surgery. Many devices have been designed and used for many, many years in applying the Ponseti technique. Currently used devices that apply the Ponseti technique are shown in U.S. Pat. No. 7,267,657. In this patent, there are disclosed improvements in such devices which provide for quick release of the shoes from the abduction bar and which also provide a method for varying the abduction angle and locking it in place at a selected angle. Devices of this type have been extremely successful and are widely used by those who treat patients using the Ponseti technique. However, the devices allow the user limited movement in the horizontal and vertical planes. Typically the user must pivot on his or her feet to move forward or backward.

Those embodiments that do allow for greater mobility in the horizontal and vertical planes such as U.S. Pat. No. 8,361,004, require a complex system of pivot points. Additionally, the rigid foot abduction apparatuses make any movement difficult for the user. There is; therefore, a need for an improved orthosis that allows greater mobility in the horizontal and vertical planes for use in treating club feet and other gait issues using the Ponseti technique that rely on a flexible bar that can bend but then return to its original shape.

SUMMARY OF THE INVENTION

The improved abduction apparatus system for correcting gait issues allows the user, typically a patient with a club foot, greater mobility while wearing the brace. A flexible elongated bar is shaped to provide a particular angle for treating clubfoot while allowing a user to bend the elongated bar while crawling or walking. The elongated bar after bending resumes its original shape after the user no longer exerts a force on the elongated bar. Several embodiments of the invention are possible to obtain the preferred result.

A first embodiment consists of an elongated plastic bar with connection means on both ends of the elongated bar. A first end is then attached to a left plate and a second end is attached to a right plate. The plates are attached to the elongated bar such that the angle of outward rotation is maintained for treating the ailment of clubfoot. The selected angle of outward rotation may be maintained once the footplates are firmly secured to shoe receiving members. The user of the foot abduction apparatus can lift up a particular foot in the vertical plane due to the flexibility of the elongated bar. Similarly, the user may achieve horizontal movement by manipulating the device by applying a force that temporarily bends the elongated bar. After the force is no longer applied by the user, the elongated bar returns to its original shape. The same embodiment also allows a user to more easily crawl if the user is unable to walk.

Other embodiments utilize an elongated bar that directly to the shoe receiving members via a slide and clip mechanism. Furthermore, in another embodiment, the elongated bar is in two pieces that are joined near the middle of the elongated bar.

DETAILED DESCRIPTION

Figure 1:
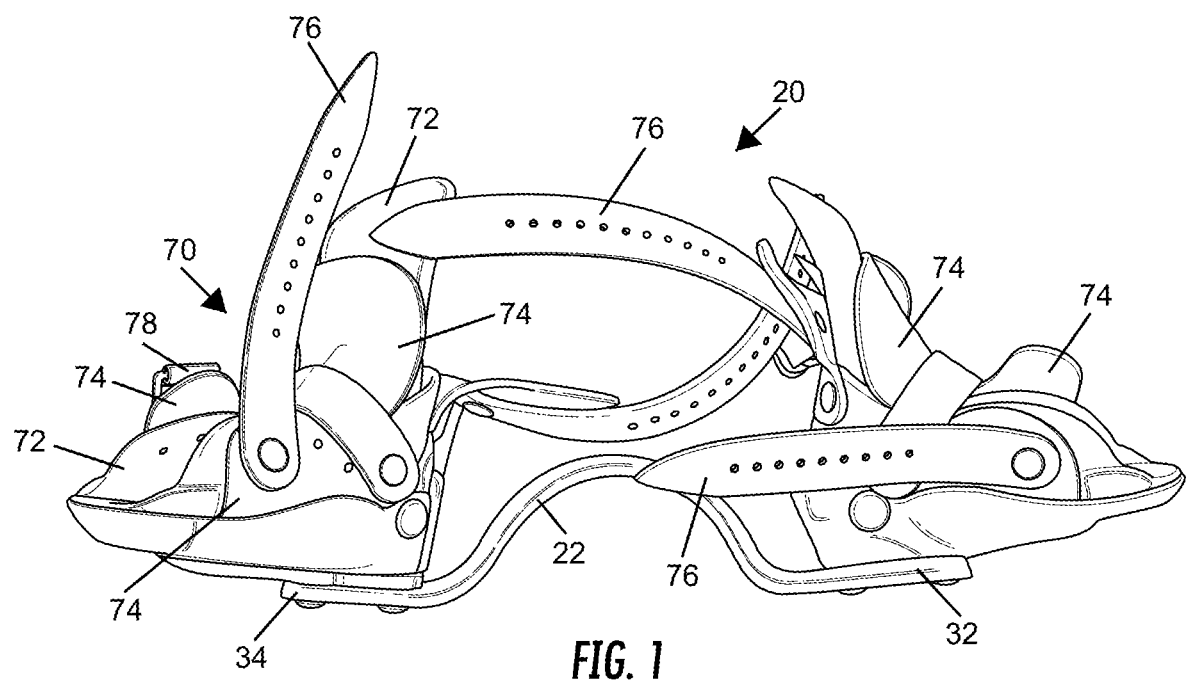
FIG. 1 is a perspective view generally of the front side of a first embodiment of a flexible foot abduction apparatus.
Figure 2:
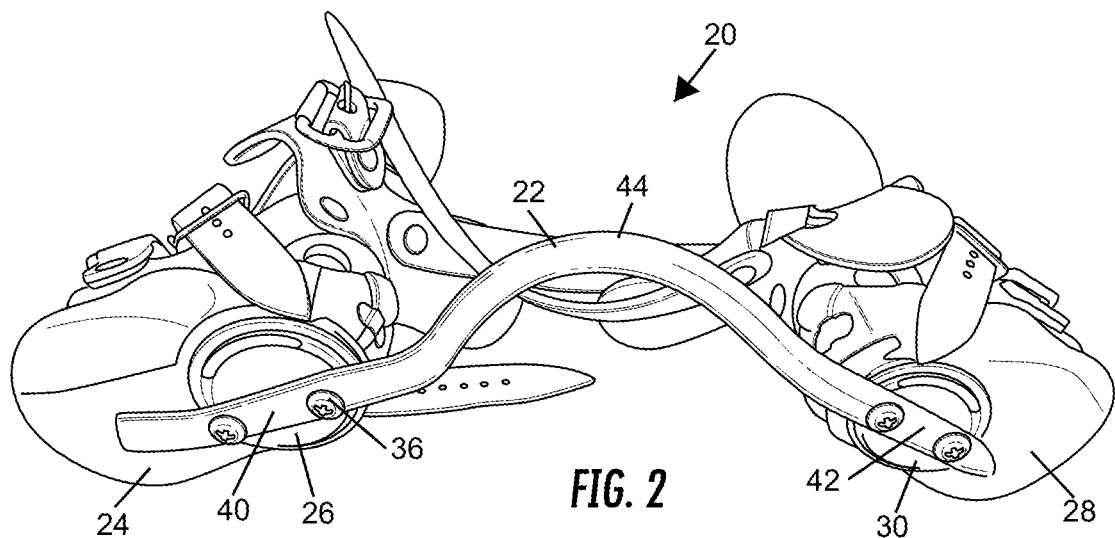
FIG. 2 is a perspective view generally of the back side of the first embodiment.
Figure 3:
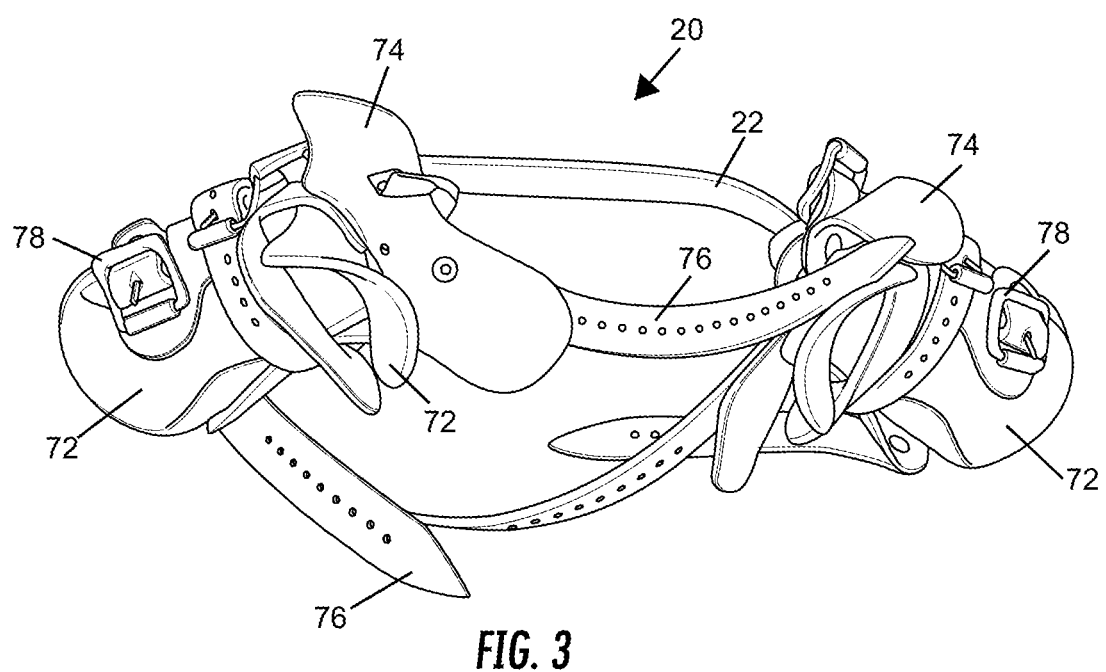
FIG. 3 is a top view of the first embodiment.

Now referring to the drawings, FIGS. 1-3 shows a flexible foot abduction apparatus 20 comprising an elongated member 22, a left shoe receiving member 24, a left plate 26, a right shoe receiving member 28 and a right plate 30. The apparatus 20 allows the user of the device to momentarily displace a first position of the apparatus 20 and allow movement of the left and right shoe receiving members 24 and 28 in both a vertical plane and horizontal plane. The elongated member 22 is made of a shape memory material that allows the vertical and horizontal movement.

The elongated member 22 has a first end 32 and a second end 34. The first end 32 is attachable to the left plate 26 via fasteners 36. In the embodiment shown in FIGS. 1-3, the fasteners 36 are screws that attach through the elongated member 34 and insert into the left plate 26. The second end 34 of the elongated member 22 is attached to the right plate 30 in the same manner as the first end 32 is attached to the left plate 26.

The elongated member 22 comprises a first portion 40, a second portion 42 and a middle portion 44 between the first portion 40 and second portion 42. The middle portion 44 is elevated above the first portion 40 and the second portion 42. This shape and features of the elongated member 22 allow a greater degree of flexibility in the horizontal and vertical planes than a straight elongated bar. This then in turn allows a greater range of motion for a user of the device.

Figure 6:
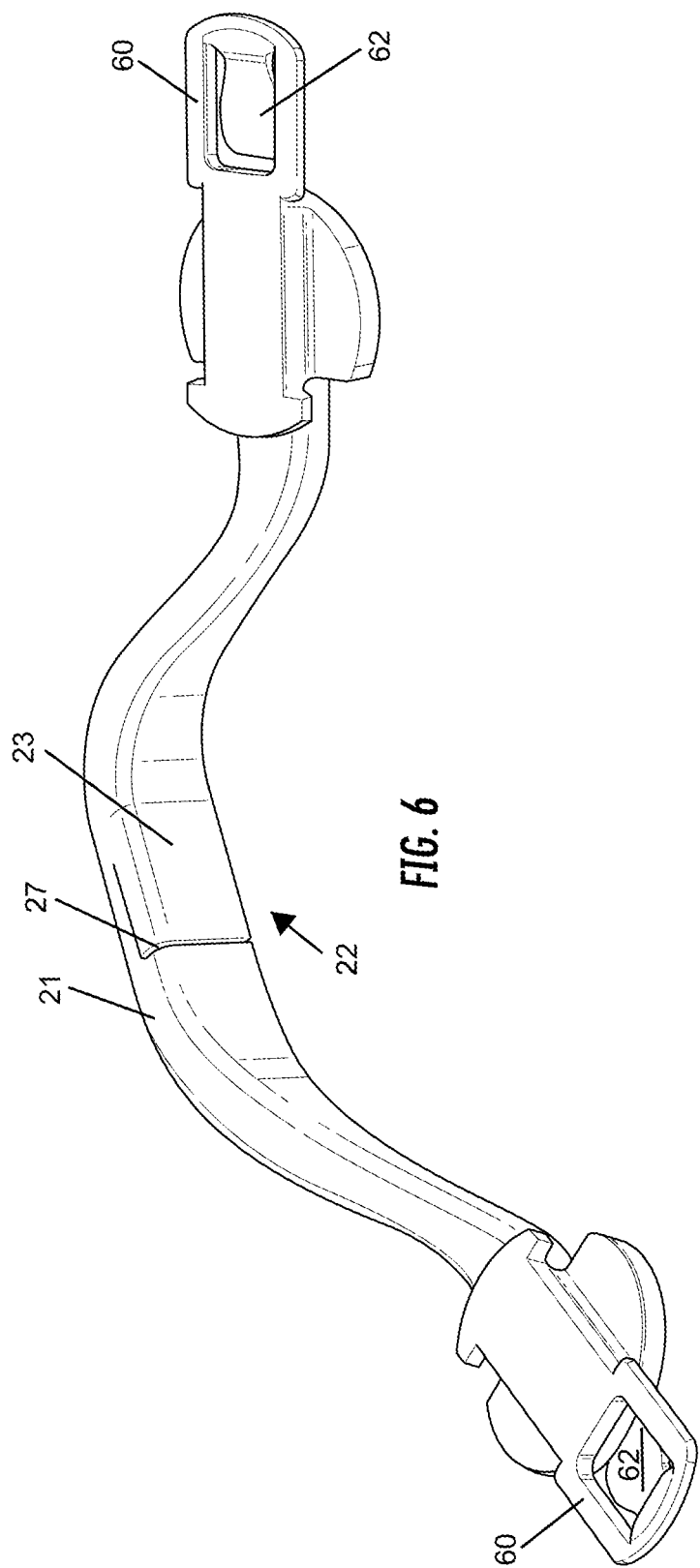
FIG. 6 is a perspective view of a second embodiment in which the flexible bar is made of two pieces and the fastening means is a sliding clip.

Again referring to FIGS. 1-3, the left plate 26 and right plate 30 each have a clip 60 feature similar to the one shown in FIG. 6 which shows a tab 62 as part of the clip 60. The left shoe receiving member 24 and the right shoe receiving member 28 each have a slot in which the clip 60 slides into. The tab 62 is flexible and is secured by a portion of the slot. This type of fastener is well known in the art. In order to separate the plate from the shoe receiving member, a user simply pushes on the tab 62 and pulls the plate opposite of the shoe receiving member. In an alternative embodiment shown in FIG. 6, the plates are omitted and the first end 32 and the second end 34 of the elongated member 22 are designed to incorporate the clip 60 design described above. Accordingly, the first end 32 is directly clipped into the left shoe receiving member 24, and the second end 34 is directly clipped into the right shoe receiving member 28.

A shoe 70 comprises a boot 72 that is preferably made of a pliable material and is attached to one of the left shoe receiving member 24. A second shoe 70 is attached to the right shoe receiving member 28. Preferably the boot 72 is made of silicone and an adhesive secures the boot 72 to the receiving member 24 or 28. A cover 74 wraps around a portion of the boot 72 and is preferably made of a felt material. Straps 76 and buckles 78 are utilized to secure a user's foot in the shoe 70. Alternatively, a user could leave his or her existing footwear on and secure the shoe 70 directly over the footwear.

Figure 4:
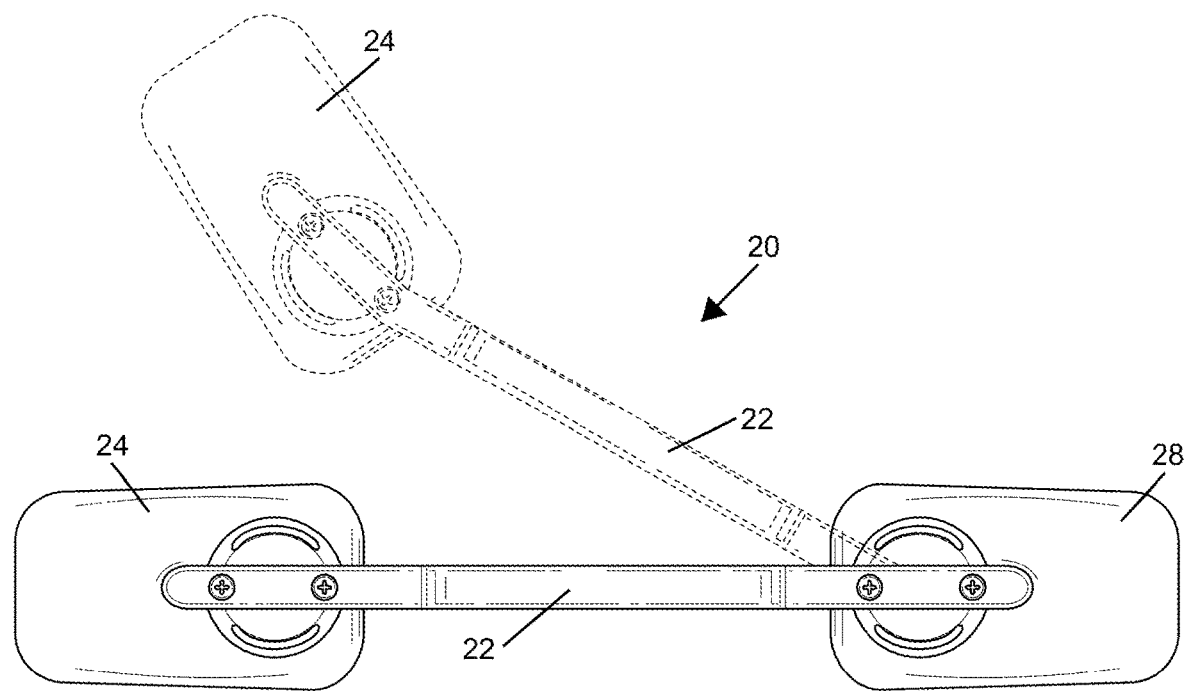
FIG. 4 is a bottom view of the first embodiment showing the embodiment in a first position and a second position and demonstrating movement in a horizontal plane.
Figure 5:
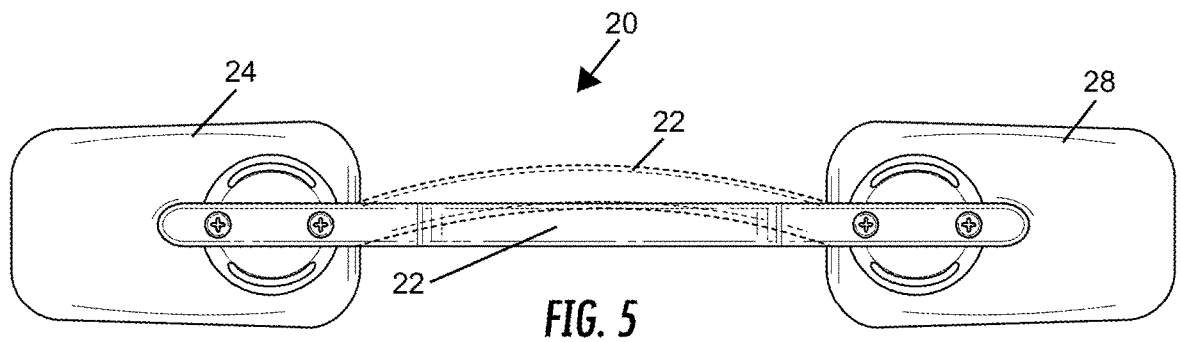
FIG. 5 is a bottom view of the first embodiment showing the embodiment in a first position and a second position and demonstrating movement in a vertical plane.

In use, a user of the flexible foot abduction apparatus 20 (device) inserts his or her feet into the shoes 70 and uses the straps 76 and buckles 78 to secure his feet. The elongated bar 22 is premade to hold the users feet in an outward angle to treat the clubfoot. The user can then generate force on the elongated bar 22 such that the user can temporarily bend the elongated bar 22 and lift one foot in a vertical plane and/or move a foot in a horizontal plane. This allows the user to walk or crawl more easily while wearing the device 20. This movement is best seen in FIGS. 4 and 5. FIG. 4 demonstrates movement of device 20 in a horizontal plane, while FIG. 5 shows flexing of the elongated bar 22 during movement in a vertical plane. Once the user stops exerting the force necessary to bend the elongated bar 22, the elongated bar 22 will return to its original premade shape. Accordingly, the outward angle used to treat the clubfoot ailment will be returned. During the course of treatment, different flexible bars with different outward angles can be attached to treat the clubfoot ailment.

FIG. 6 shows an embodiment of the device 20 in which the elongated member 22 is made of two separate pieces, a first member 21 and a second member 23. The two are then joined together via any well-known means. A gap 27 allows greater flexibility of the elongated bar 22. Additionally, the first member 21 and the second member 23 can be joined such that each member 21, 23 pivot around the other. Accordingly, a user to the device can move more easily in the vertical plane.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is:

1. A flexible foot abduction apparatus allowing vertical and horizontal movement comprising:
    an elongated member comprising a first end and a second end;
    a left plate;
    the left plate selectively attachable to the first end;
    a right plate;
    the right plate selectively attachable to the second end;
    the elongated member having a first portion and a second portion;
    the elongated member having a middle portion between the first portion and second portion;
    the middle portion above the first portion and the second portion;
    wherein the middle portion is configured to allow a user to move the first end in both a horizontal plane and a vertical plane relative to the second end;
    the elongated member having an original shape;
    the elongated member bendable to a second shape when a force is applied by the user;
    the elongated member made of a shape memory material wherein the elongated member reforms to the original shape upon removal of the force.

2. The flexible foot abduction apparatus of claim 1 further comprising:
    a left shoe receiving member.

3. The flexible foot abduction apparatus of claim 2 further comprising:
    a right shoe receiving member.

4. The flexible foot abduction apparatus of claim 3, wherein:
    the left plate is attached to the left shoe receiving member;
    a shoe is attached to the left shoe receiving member;
    the shoe comprising a boot,
    the boot made of a pliable material.

5. The flexible foot abduction apparatus of claim 4, wherein:
    the right plate is attached to the right shoe receiving member;
    a second shoe is attached to the right shoe receiving member.

6. The flexible foot abduction apparatus of claim 5, wherein:
    the elongated member is attached to the left plate wherein the left plate makes a specific angle to the elongated member configured to treat the ailment of club foot.

7. The flexible foot abduction apparatus of claim 6, wherein:
    the shoe further comprises a cover made of a pliable material;
    the cover is attached to the boot.

8. The flexible foot abduction apparatus of claim 7, wherein:
    the cover comprises a plurality of adjustment straps configured to selectively strap in a foot of a user to the apparatus.

9. A flexible foot abduction apparatus allowing vertical and horizontal movement comprising:
    an elongated member comprising a first end and a second end;
    a left plate;
    the left plate selectively attachable to the first end;
    a right plate;
    the right plate selectively attachable to the second end;
    the elongated member is attached to the left plate wherein the left plate makes a specific angle to the elongated member configured to treat the ailment of club foot;
    the elongated member having an original shape;
    the elongated member bendable to a second shape when a force is applied by the user of the apparatus;
    the elongated member made of a shape memory material wherein the elongated member reforms to the original shape upon removal of the force.

10. The flexible foot abduction apparatus of claim 9, wherein:
    the elongated member has a first portion and a second portion;
    the elongated member has a middle portion between the first portion and second portion;
    the middle portion above the first portion and the second portion;

wherein the middle portion is configured to allow a user to move the first end in both a horizontal plane and a vertical plane relative to the second end.

11. The flexible foot abduction apparatus of claim 10, wherein:
the left plate is attached to a left shoe receiving member.

12. The flexible foot abduction apparatus of claim 11, wherein:
the right plate is attached to a right shoe receiving member.

13. The flexible foot abduction apparatus of claim 12, further comprising:
a shoe;
the shoe comprising a boot,
the boot made of a pliable material.

14. The flexible foot abduction apparatus of claim 13, wherein:
the left shoe receiving member is attached to the left plate.

15. The flexible foot abduction apparatus of claim 14, wherein:
the shoe further comprises a cover made of a pliable material;
the cover is attached to the boot.

16. The flexible foot abduction apparatus of claim 15, wherein:
the cover comprises a plurality of adjustment straps configured to selectively strap in a foot of a user to the apparatus.

17. A flexible foot abduction apparatus comprising:
an elongated member comprising a first end and a second end;
a left plate;
the left plate selectively attachable to the first end;
a right plate;
the right plate selectively attachable to the second end;
the elongated member having a first portion and a second portion;
the elongated member having a middle portion between the first portion and second portion;
the middle portion above the first portion and the second portion;
wherein the middle portion is configured to allow a user to move the first end in both a horizontal plane and a vertical plane relative to the second end;
the elongated member having an original shape;
the elongated member bendable to a second shape when a force is applied by the user of the apparatus;
the elongated member made of a shape memory material wherein the elongated member reforms to the original shape upon removal of the force.

18. The flexible foot abduction apparatus of claim 17, wherein:
the left plate is attached to a left shoe receiving member;
the right plate is attached to a right shoe receiving member.

19. The flexible foot abduction apparatus of claim 18 further comprising:
a shoe;
the shoe comprising a boot,
the boot made of a pliable material.

20. The flexible foot abduction apparatus of claim 19, wherein:
the shoe further comprises a cover made of a pliable material;
the cover is attached to the boot;
the cover comprises a plurality of adjustment straps configured to selectively strap in a foot of a user to the apparatus.

* * * * *